(12) United States Patent
Cude

(10) Patent No.: US 7,815,606 B2
(45) Date of Patent: Oct. 19, 2010

(54) SYRINGE ADAPTER SYSTEM AND METHOD OF CLEANING THE ADAPTER

(75) Inventor: J. Michael Cude, Woodburn, KY (US)

(73) Assignee: Coeur, Inc., Lebanon, TN (US)

( * ) Notice: Subject to any disclaimer, the term of this patent is extended or adjusted under 35 U.S.C. 154(b) by 307 days.

(21) Appl. No.: 11/568,225

(22) PCT Filed: Apr. 25, 2005

(86) PCT No.: PCT/IB2005/051345

§ 371 (c)(1),
(2), (4) Date: Sep. 26, 2007

(87) PCT Pub. No.: WO2005/101967

PCT Pub. Date: Nov. 3, 2005

(65) Prior Publication Data

US 2008/0125714 A1    May 29, 2008

Related U.S. Application Data

(60) Provisional application No. 60/565,122, filed on Apr. 23, 2004.

(51) Int. Cl.
*A61M 37/00* (2006.01)

(52) U.S. Cl. .................... 604/154; 604/121

(58) Field of Classification Search .................. 604/151, 604/152, 154, 228, 240, 535
See application file for complete search history.

(56) References Cited

U.S. PATENT DOCUMENTS

| 4,695,271 | A  | * | 9/1987  | Goethel ..................... 604/506 |
| 5,279,569 | A  | * | 1/1994  | Neer et al. .................. 604/154 |
| 5,520,653 | A  | * | 5/1996  | Reilly et al. ................ 604/152 |
| 5,947,929 | A  | * | 9/1999  | Trull ......................... 604/152 |
| 6,080,136 | A  | * | 6/2000  | Trull et al. .................. 604/218 |
| 6,336,913 | B1 | * | 1/2002  | Spohn et al. ................ 604/154 |
| 6,821,013 | B2 | * | 11/2004 | Reilly et al. ............. 366/162.3 |
| 2001/0016962 | A1 | * | 8/2001 | Moore et al. ............. 15/104.16 |
| 2004/0133162 | A1 | * | 7/2004 | Trocki et al. ................ 604/131 |

* cited by examiner

Primary Examiner—Nicholas D Lucchesi
Assistant Examiner—Gerald Landry, II
(74) Attorney, Agent, or Firm—Hahn, Loeser & Parks, LLP

(57) ABSTRACT

A syringe adapter assembly comprises an adapter body and a ram extender. In one embodiment, the adapter body (12) is attached to an injector by a rear connector plate (50). In a second aspect, the adapter body (12, 122) may comprise a drain hole (130) and/or sealing ring (140). In another aspect, the invention comprises a cleaning member (200) having a body (204) and a plurality of cleaning members (210, 220, 230) extending therefrom.

17 Claims, 10 Drawing Sheets

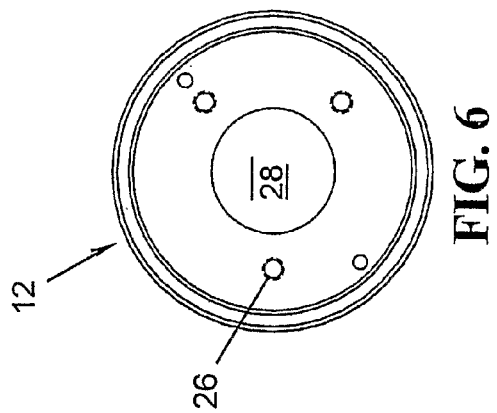
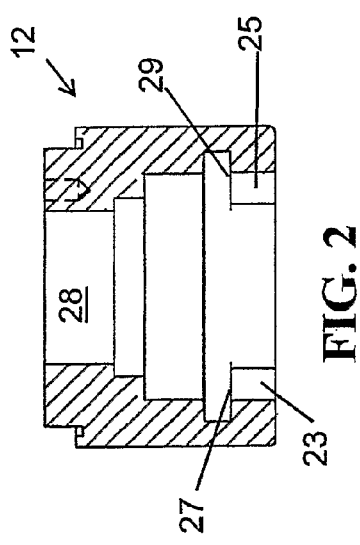
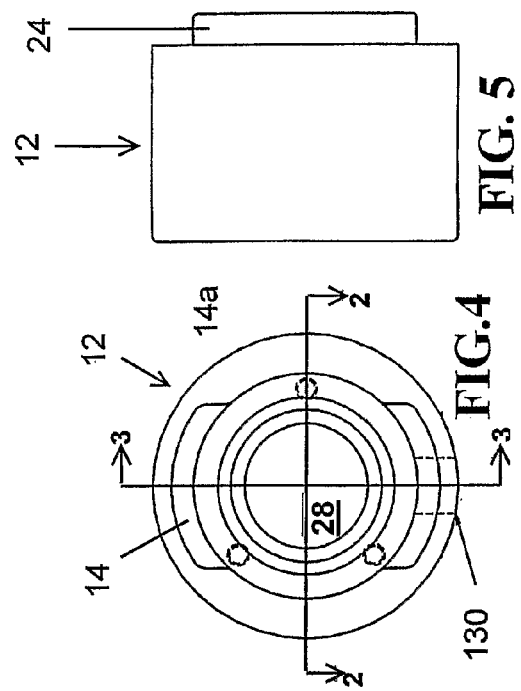
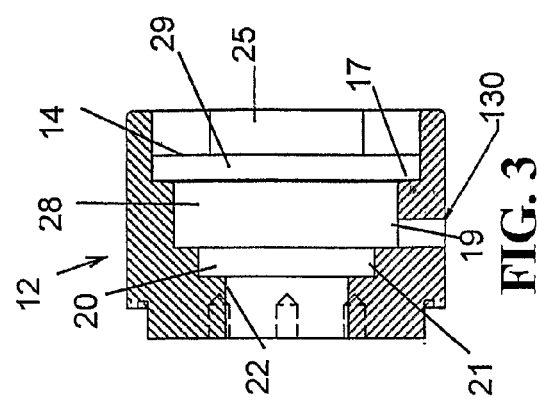
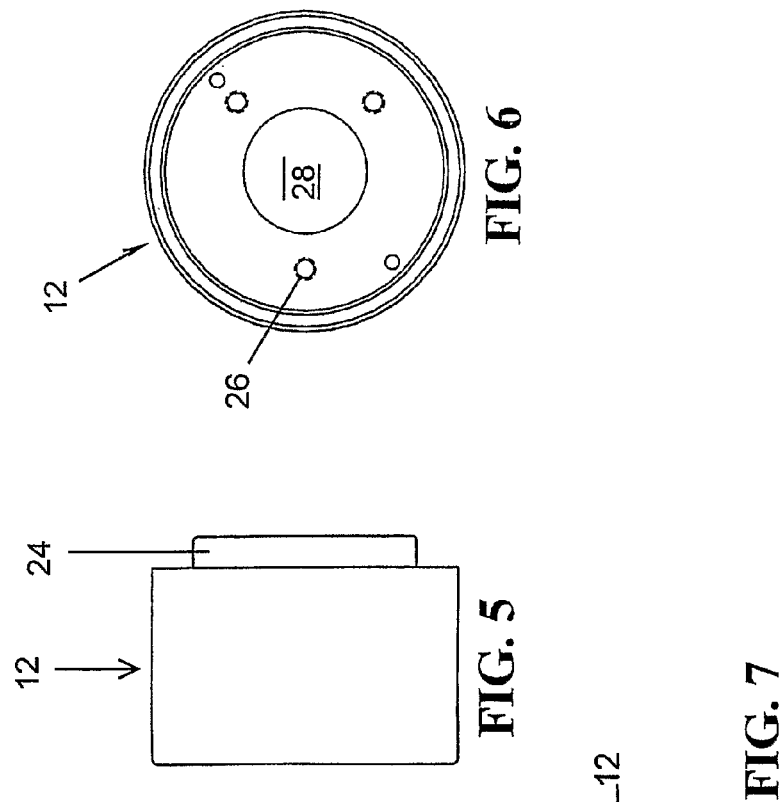

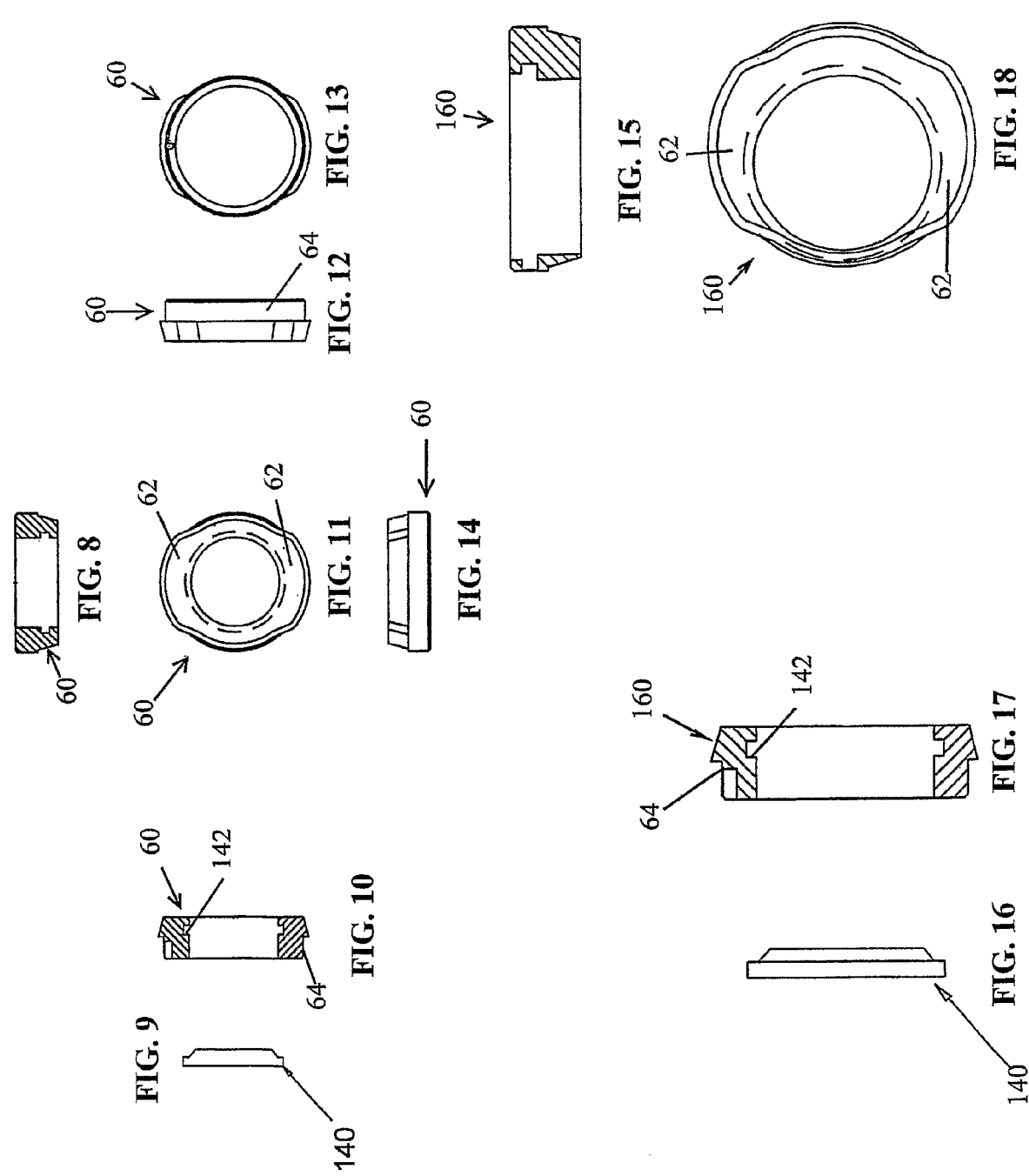

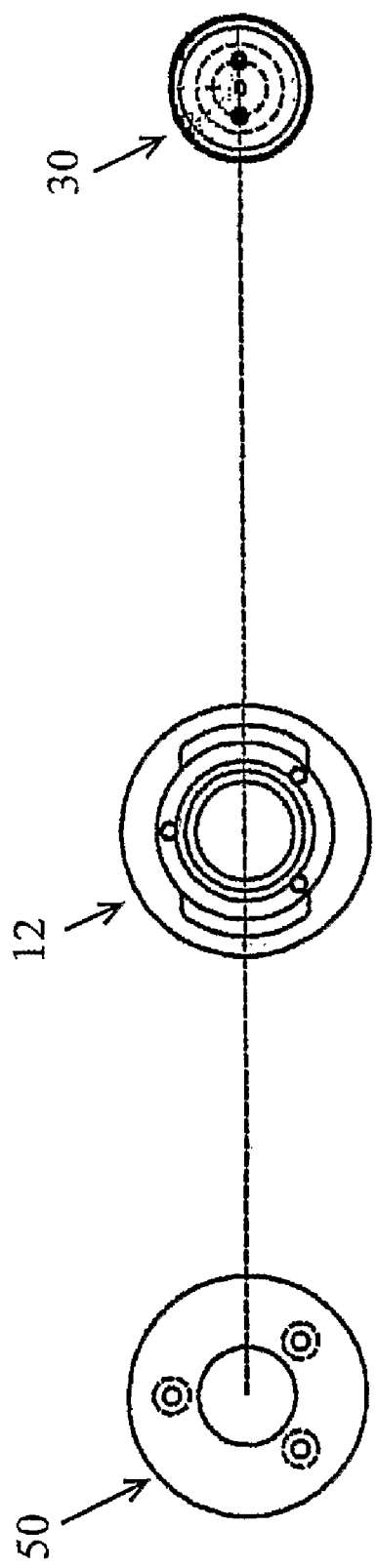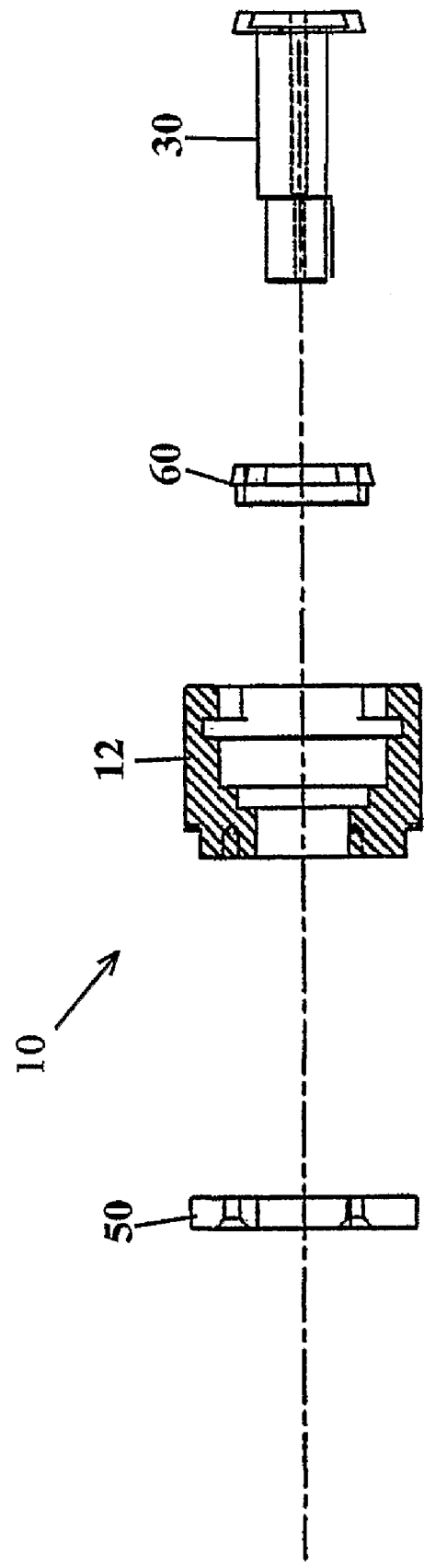
FIG. 19
FIG. 20

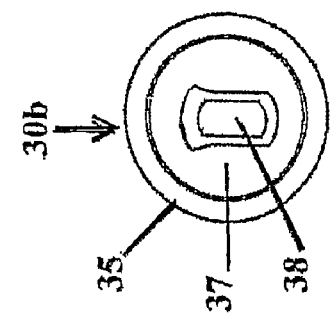
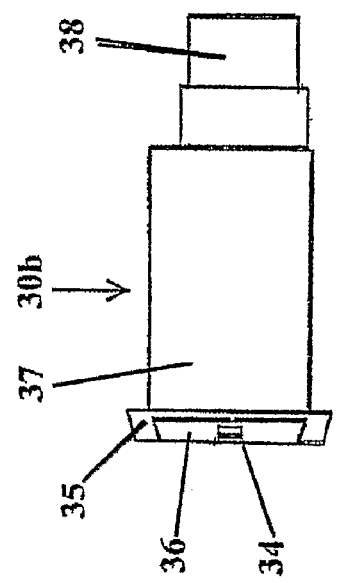
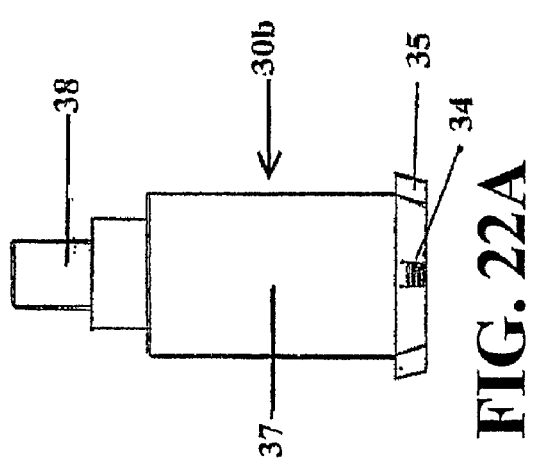
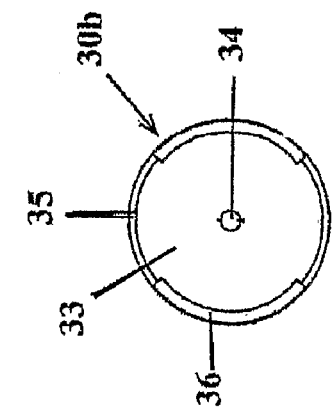

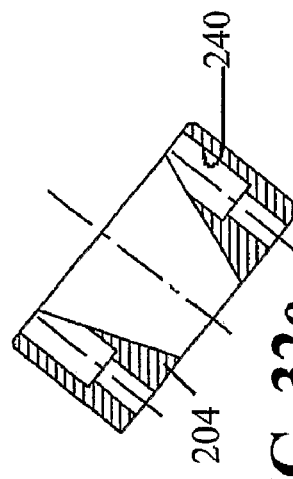
FIG. 32e
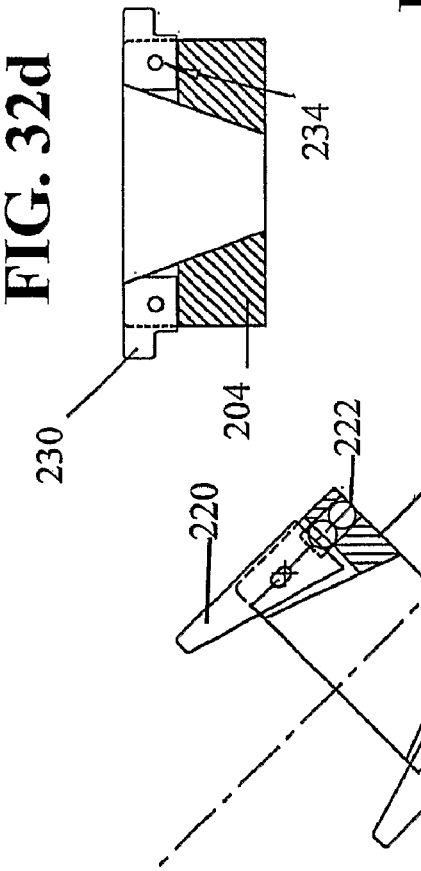
FIG. 32d
FIG. 32c
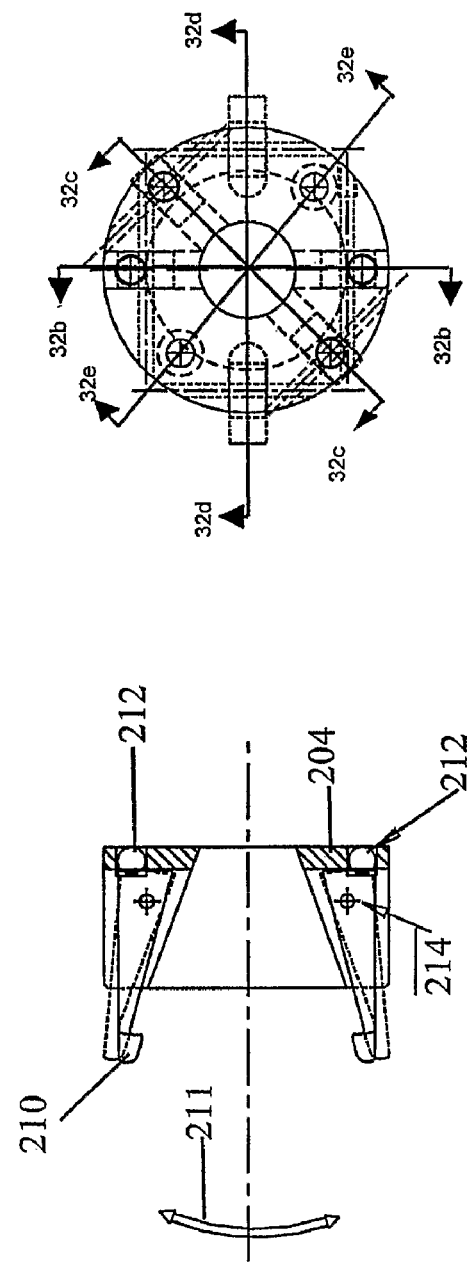
FIG. 32a
FIG. 32b

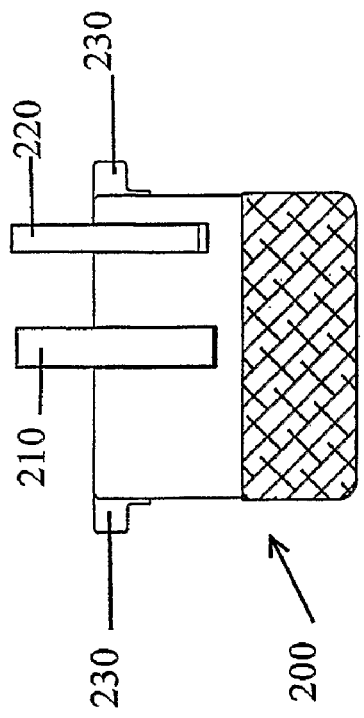
FIG. 33
FIG. 34
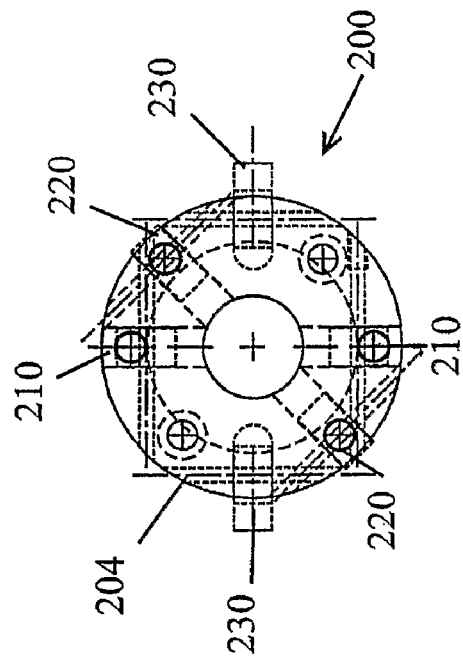
FIG. 35

SYRINGE ADAPTER SYSTEM AND METHOD OF CLEANING THE ADAPTER

TECHNICAL FIELD

The present invention relates to syringe adapters, and more specifically to syringe adapters having a drain and sealing assembly, and a method and apparatus for cleaning the adapter.

BACKGROUND OF THE INVENTION

Syringe adapters are known in the art. Syringe adapters typically comprise an adapter body that is attachable to a power injector for injecting fluids. One such adapter body 122 with lifting ring 60 is disclosed in U.S. Pat. No. 6,080,136, and illustrated in FIG. 1.

One problem associated with syringe adapters is that, over time, the grooves of the adapter may become soiled with dried contrast fluid. Another problem is that fluid within the adapter body cannot drain from the adapter. Still another problem is that the user cannot introduce fluid into the adapter because the fluid may escape into the injector and thereby cause damage to the injector. Given these problems, until now there has been no easy way to clean the adapter, short of removing it from the injector. As such, there is a need for a syringe adapter that can drain contrast fluid and can be cleaned while attached to the injector. Accordingly, the present invention is hereby submitted.

SUMMARY OF THE INVENTION

In one aspect, the present invention comprises a syringe adapter body having a drain hole located in an interior portion of the adapter body. The drain hole allows fluid that is present within the adapter body to drain from the adapter.

In another aspect, the present invention comprises a seal that is located within the central bore of the adapter body to help prevent fluid introduced into the adapter body from penetrating into the injector.

In a third aspect, the present invention comprises a cleaning apparatus that can be inserted into the front of the injector and rotated to clean the various shoulders and grooves of the adapter. The cleaning apparatus may comprise a handle, a body, and three pair of cleaning blades extending from the body.

In a fourth aspect, the present invention comprises a syringe adapter assembly having an adapter body, a rear connector plate, and a ram extender.

SUMMARY OF THE DRAWINGS

FIG. 2 is a cross-sectional view of a second embodiment of a syringe adapter body, taken on line 2-2 of FIG. 4.

FIG. 3 is a cross-sectional view of the syringe adapter body of FIG. 2, taken on line 3-3 of FIG. 4, illustrating a drain hole, in accordance with a preferred embodiment of the present invention.

FIG. 4 is a front view of the syringe adapter body of FIG. 2.

FIG. 5 is a right side view of the syringe adapter body of FIG. 2.

FIG. 6 is a rear view of the syringe adapter body of FIG. 2

FIG. 7 is a bottom view of the syringe adapter body of FIG. 2, illustrating the drain hole.

FIG. 8 is a cross-sectional view of a lifting ring.

FIG. 9 is a side view of a bore seal.

FIG. 10 is a side cross-sectional view of the lifting ring of FIG. 8

FIG. 11 is a front view of the lifting ring of FIG. 8.

FIG. 12 is a side view of the lifting ring of FIG. 8.

FIG. 13 is a rear view of the lifting ring of FIG. 8.

FIG. 14 is a side view of the lifting ring of FIG. 8.

FIG. 15 is a side cross-sectional view of a second embodiment of a lifting ring, the lifting ring being offset from the bore.

FIG. 16 is a bore seal for use with the lifting ring of FIG. 15.

FIG. 17 is a side cross sectional view of the lifting ring of FIG. 15.

FIG. 18 is a front view of the lifting ring of FIG. 15.

FIG. 19 is a schematic view of the components of the syringe adapter assembly.

FIG. 20 is a side exploded view of the components of the syringe adapter assembly.

FIG. 22A is a side view of a second embodiment of a ram extender.

FIG. 22B is a front view of the ram extender shown in FIG. 22A.

FIG. 22C is a right side view of the ram extender shown in FIG. 22A.

FIG. 22D is a back view of the ram extender shown in FIG. 22A.

FIG. 32a-e is a schematic representation illustrating a rear view of the adapter cleaner body and various cross-sections therethrough illustrating the different cleaning blade alignments relative thereto.

FIG. 33 is a side view of an adapter cleaner in relation to rear schematic view FIG. 35.

FIG. 34 is a second side view of an adapter cleaner in relation to rear schematic view FIG. 35.

FIG. 35 is a rear schematic view of the adapter cleaner.

DETAILED DESCRIPTION

Figure 1:
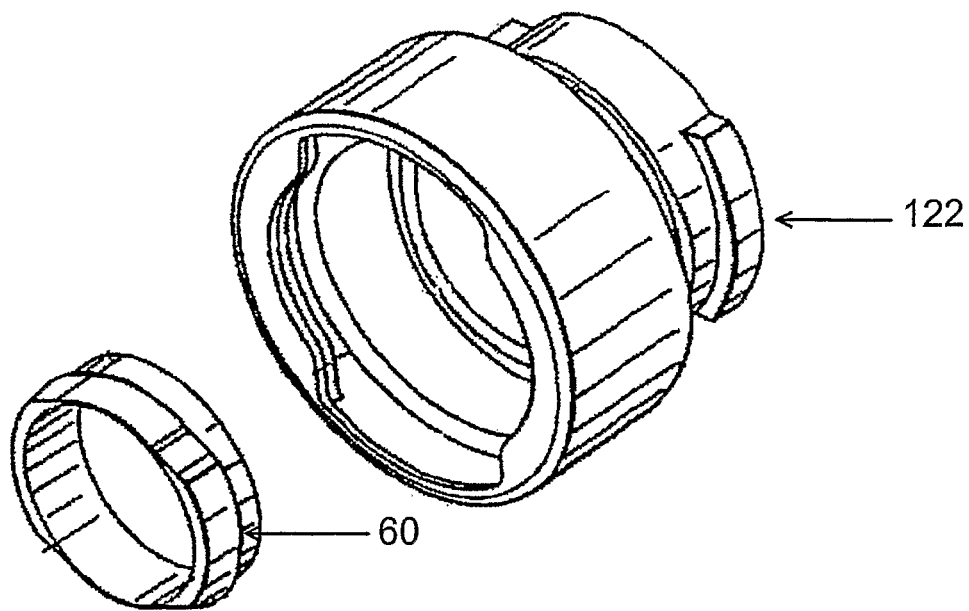
FIG. 1 is a perspective view of a type of syringe adapter that may be utilized with an embodiment of the present invention.

An exemplary embodiment of a syringe adapter assembly 10 is illustrated in FIGS. 19-20. The syringe adapter assembly 10 may comprise an adapter body 12, a lifting ring 60, ram extender 30, a syringe or rear connector plate 50, and sealing ring or bore seal 140 (shown in FIGS. 9 and 16). A second embodiment of a syringe adapter assembly 112, as described in U.S. Pat. No. 6,080,136, is illustrated in FIG. 1. The disclosure of U.S. Pat. No. 6,080,136 is hereby incorporated by reference.

An embodiment of syringe adapter body 12 is illustrated in FIGS. 2-7. See also PCT International application no. PCT/IB2004/050493, the disclosure of which is incorporated by reference. The outer surface of the adapter body 12 may be cylindrical, although the outer surface may be any of a plurality of shapes without deviating from the scope of the present invention. The adapter body 12 may have mounted thereon or integrally formed therewith a rear cylindrical extension 24. An O-ring may be positioned at the junction of adapter body 12 and rear cylindrical extension 24. A central bore 28 may extend through the adapter body 12. The central bore 28 may receive a rain extender 30, illustrated in FIGS. 21A-D and 22A-D, which is adapted to couple to the drive ram of the injector. The central bore 28 may be bound in the rear cylindrical extension 24 by first bounding wall 22. First bounding wall 22 extends forwardly from the rear cylindrical extension 24. Without the lifting ring 60 mounted in the adapter body 12, the first bounding wall 22 terminates at shoulder 21. The lifting ring 60, illustrated in FIGS. 17-22, may be mounted within the area defined by shoulder 21 and lifting ring bounding wall 20. The interior diameter of lifting ring 60 may be substantially equal to the first bounding wall 22. As such, when the lifting ring 60 is mounted within adapter body 12, the first bounding wall 22 operably extends to shoulder 19.

The central bore 28 may also be bound in the main body by second bounding wall 18 and by third bounding wall 14. The first bounding wall 22 is, in the exemplary embodiment, of smaller diameter than second bounding wall 18, and the second bounding wall 18 is of smaller diameter than third bounding wall 14.

The adapter may include front slot opening 14a communicating with the third bounding wall 14 of central bore 28 and forming therewith diametrally opposed grooves 27 and 29, and thereby defining diametrally opposed retention flange portions 23 and 25 transverse to the slot opening, for engagement with a syringe, as described below. However, any structure is contemplated for attachment of a syringe to the adapter.

As used herein, the term "diametrally opposed" means that the relevant structural elements are located at opposite sides of a cylindrical or circular element or member of the appertaining apparatus. The diametrally opposed elements or members are thus symmetrically arranged with respect to an associated diameter of the cylindrical or circular part or structure with which they are associated.

The syringe may include a main cylindrical barrel enclosing an inner volume, which in use of the syringe is filled with contrast media or other solution or liquid to be dispensed through the distal end of the syringe. At its distal end, the syringe may be provided with threading in its interior surface, for connection of the distal end of the syringe to a catheter by means of luer-lock or other conventional coupling means.

The interior volume of the syringe is bounded by an interior wall surface. At the proximal end of the syringe is interiorly disposed a plunger. The plunger is of generally converging shape at its distal end, and includes an outer circumferentially continuous edge (side) surface which contacts the inner wall surface of the syringe. The plunger may further include at least two diametrally opposed arrays of spaced-apart flexible resilient engagement members.

At the proximal end of the syringe on the exterior surface thereof may be provided diametrally opposed flange or lug members for engaging and locking the syringe to the adapter 10.

A first exemplary embodiment of the ram extender 30a is illustrated in FIGS. 21a-21d. A second embodiment of ram extender 30b is illustrated in FIGS. 22a-2d. The ram extender 30a or 30b may attach to the ram of the injector. Depending on the model of the injector, one of the ram extenders 30a or 30b, may be used. It is contemplated that other configurations of ram extenders could be utilized, the configuration being dependent on the particular injector and the particular syringe to be used. Before attaching either ram extender 30a or 30b, grippers or jaws or other syringe-attachment parts on the existing injector may need to be removed from the drive ram. Ram extender 30a is attached to the drive ram via screws that are inserted through longitudinal apertures 32 in ram extender 30a and into threaded apertures in the front of the drive ram. Ram extender 30b is attached to the drive ram of the injector via a pin or other fastener that is inserted through transverse aperture (not shown) in the ram extender and through a transverse aperture (not shown) in the drive ram of the injector. Various other embodiments of a ram extender, fasteners or means for attaching the ram extender 30a or 30b to the drive ram as are obvious to one of ordinary skill in the art are contemplated.

Figure 23:
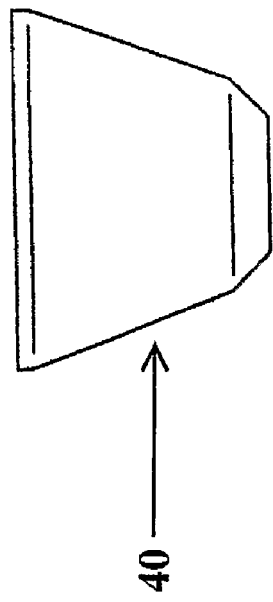
FIG. 23 is a side view of a ram tip cone.
Figure 25:
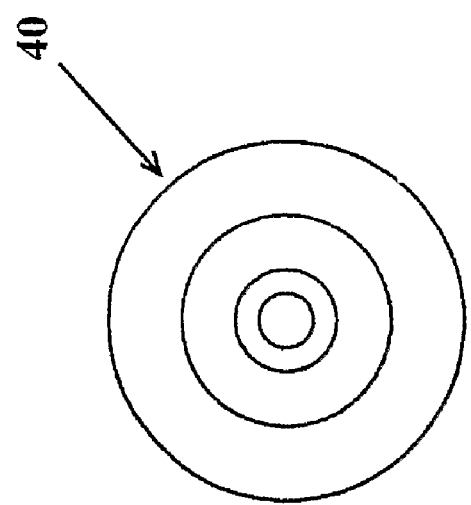
FIG. 25 is a front view of the ram tip cone shown in FIG. 23.
Figure 24:
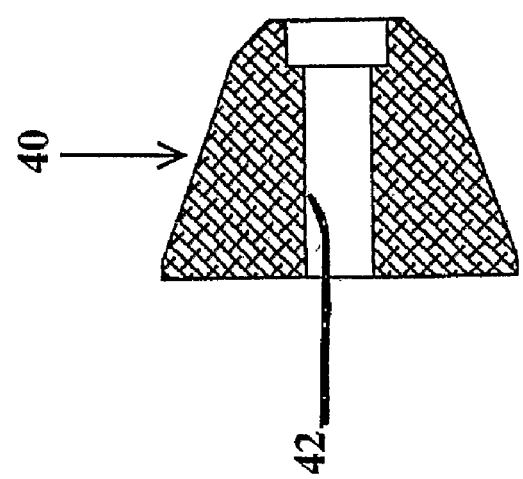
FIG. 24 is a side cross-sectional view of the ram tip cone shown in FIG. 23.
Figure 26:
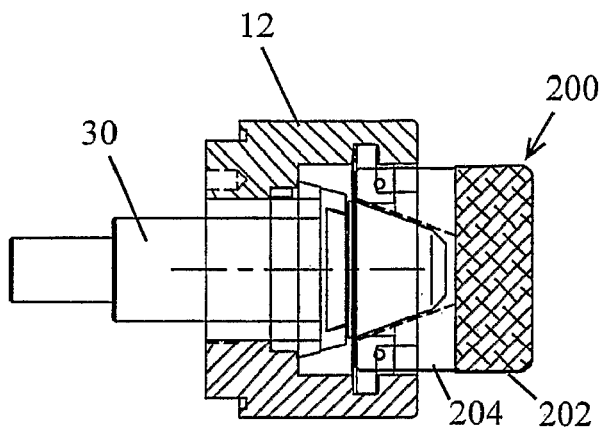
FIG. 26 is a side cross-sectional view of a syringe adapter assembly and adapter cleaner.
Figure 27:
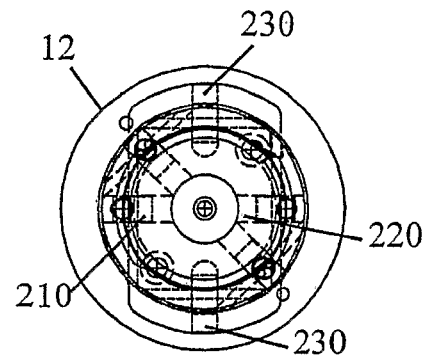
FIG. 27 is a front schematic view of FIG. 26.

Ram extender 30a and 30b are of frustoconical shape, each having a front circular surface 33 with a central threaded aperture 34 that receives a fastener for attaching the ram tip cone 40 (See FIGS. 23-25) to the ram extender 30a or 30b. The ram extender 30a or 30b additionally has a frustoconical side surface 35 with rounded-over portions 36, a cylindrical body 37, and a rear connecting extension 38. Ram tip cone 40, as illustrated in FIGS. 23-25, may attach to front circular surface 33 via at least one fastener that is received within aperture 42 and into closed-ended threaded aperture 34 in ram extender 30a or 30b. Ram tip cone 40 provides a substantially complementary shape to the rear surface of a plunger. With ram extender 30a, the ram tip cone 40 should be installed after the ram extender 30a is attached to the drive ram of the injector. With ram extender 30b, the user may attach ram tip cone 40 either before or after the ram extender 30b is attached to the drive ram of the injector.

As illustrated in FIGS. 8-18, lifting ring 60, 160 has a cylindrical collar 64 which, in one embodiment, is constructed and arranged in a press fit relationship with lifting ring bounding wall 20 of the central bore 28 in the adapter body 12. The lifting ring 60, 160 may as shown in FIGS. 18, 20, and 22, include outwardly extending shoulder elements 62 that are diametrally opposite one another, so that the lifting ring has unshouldered circumferential portions that are diametrally opposite one another and that are between the shoulder elements 62. As can be seen in FIGS. 15 and 18, the lifting ring 160 may have shoulder elements 62 that are offset from the aperture.

Figure 36:
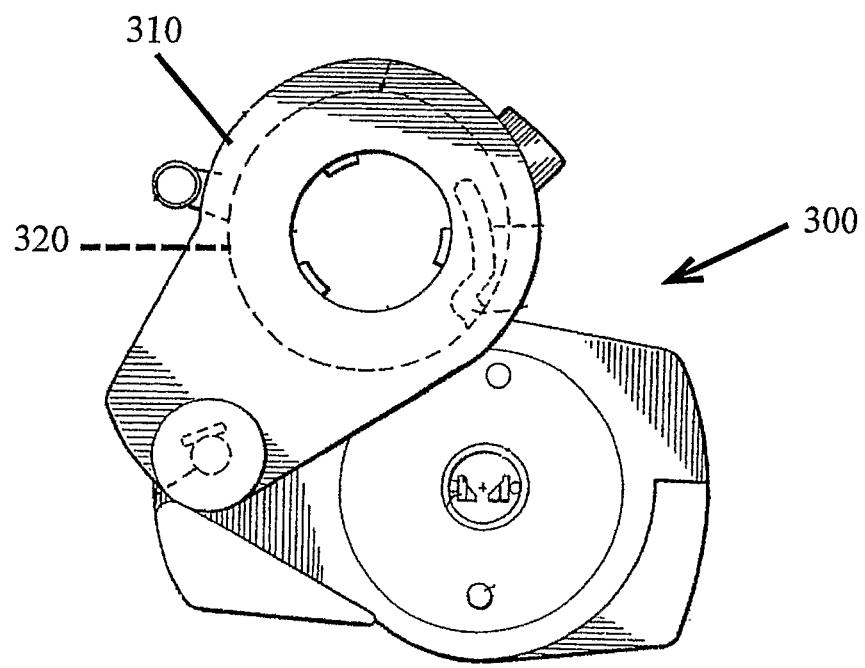
FIG. 36 is a front view of one embodiment of an injector that can be utilized with the present invention.
Figure 21D:
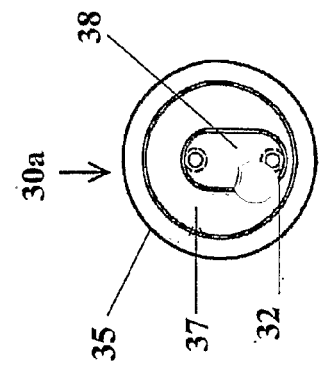
FIG. 21D is a back view of the ram extender shown in FIG. 21A.
Figure 21C:
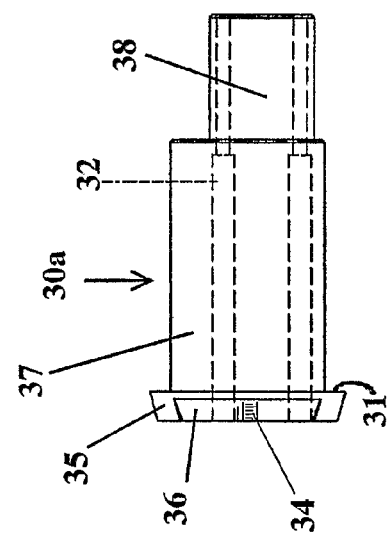
FIG. 21C is a side view of the ram extender shown in FIG. 21A.
Figure 21A:
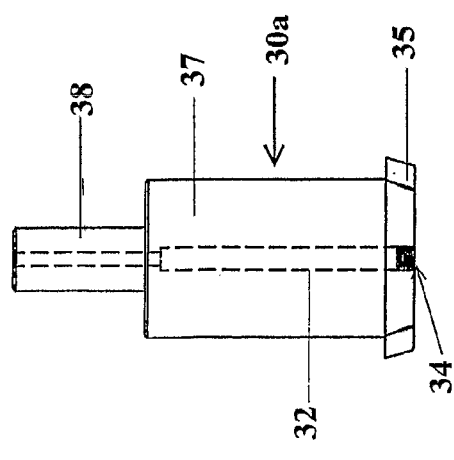
FIG. 21A is a side view of a first embodiment of a ram extender.
Figure 21B:
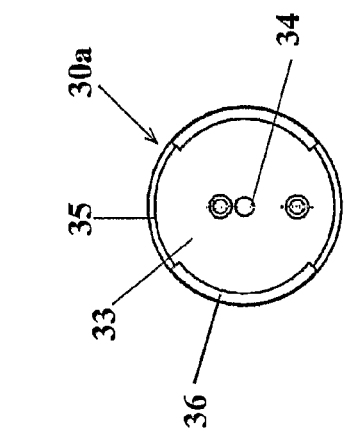
FIG. 21B is a front view of the ram extender shown in FIG. 21A.

The adapter assembly 10 is attached to the injector 300, an exemplary illustration of which is illustrated in FIG. 36, via the adapter (or rear) connector plate 50 illustrated in FIGS. 19-20. The injector may comprise rotatable door 310 having an aperture therethrough, and a recess 320 in a rear surface thereof that receives connector plate. To attach the adapter to the injector in this embodiment, the rear extension 24 is inserted into the aperture in the door 310, and rear connector plate 50 is inserted in the recess in the rear of the door. The adapter body 12 and connector plate 50 each may include complementary threaded apertures that receive fasteners, to therefore attach the adapter body 12 to the door 310.

A preferred embodiment of the adapter body 12, 122 comprises drain hole 130. Drain hole 130 preferably extends through the adapter body 12 to allow any fluid present within the adapter body 12 to drain out of the adapter body 12. It is contemplated that drain hole 130 can be used with any adapter system as is known in the art, without deviating from the scope of the present invention.

Another embodiment of the adapter system comprises seal 140, as illustrated in FIGS. 9 and 16. Seal 140 may be generally circular in shape and may be received within, for example, recess 142 in lifting ring 60, 160. Ram extender 30, in operation, extends through the aperture in the seal 140. As such, the relationship between seal 142 and ram extender 30 fluidly seals the adapter assembly 10 from the injector. For example, when the ram extender 30 is retracted, liquid can be introduced into the interior of the adapter body, and the liquid will not escape rearwardly into the main portion of the injector. As with drain hole 130, seal 140 can be utilized with any adapter system as is known in the art, without deviating from the scope of the present invention.

Another aspect of the invention comprises adapter cleaner 200. Adapter cleaner 200 may comprise knurled grip 202, and cleaner body 204. Adapter cleaner 200 may additionally comprise six cleaners or cleaning blades 210, 220, 230 for scraping and cleaning the various portions of the interior of the injector. The six cleaning blades are preferably arranged in three pair of blades, each blade of a pair of blades being diametrally opposite one another. Knurled grip 202 is preferably attached to cleaner body 204 by fasteners (not shown) extending through apertures 240. The cleaner can obviously be adapted for specific use with different adapters via changes the configuration of the cleaners, and different configurations are contemplated.

Figure 29:
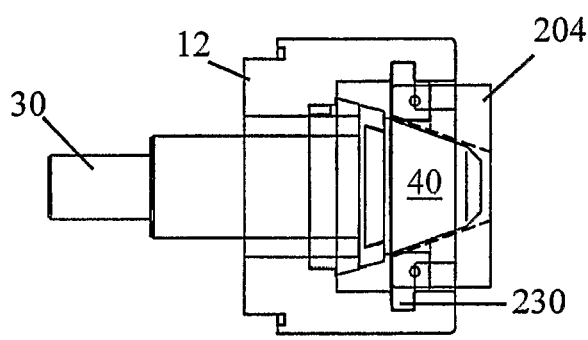
FIG. 29 is a side schematic view of FIG. 28, illustrating the flange level cleaning blades.
Figure 28:
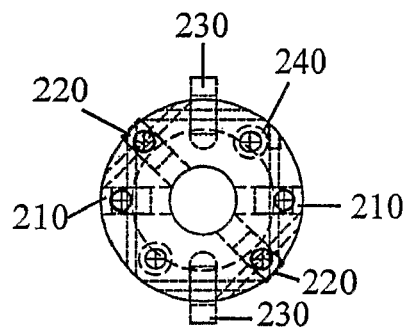
FIG. 28 is a schematic representation of the layout of the adapter cleaning blades and adapter cleaner body.

Flange level cleaning blades 230 fit within slots in cleaner body 204 and are secured to the cleaner body by pins 234. Flange level cleaning blades 230 extend radially outwardly of cleaner body 204. When adapter cleaner 200 has been inserted into central bore 28 of adapter body 12, flange level cleaning blades 230 extend into grooves 27, 29 (See FIG. 29). When the adapter cleaner 200 is rotated, flange level cleaning blades 230 clean grooves 27, 29, adjacent surfaces of flange portions 23, 25, and shoulder 17.

Figure 31:
FIG. 31 is a side schematic view of FIG. 28, illustrating the ram tip cleaning blades.

Ram tip bottom cleaning blades 210 fit within slots in cleaner body 204 and are secured to the cleaner body by pins 214. Ram tip bottom cleaning blades 210 extend axially from cleaner body 204. Compression balls 212, below ram tip bottom cleaning blades 210, bias tips of the cleaning blades radially inward as shown by arrow 211 in FIG. 32. As the adapter cleaner 200 is inserted in the central bore 28 of adapter body 12, the tips of cleaning blades 210 will encounter the ram extender 30 and move radially outward to allow the tips to pass behind the ram extender 30. The tips of ram tip bottom cleaning blades 210 will then move back radially inward, due to the bias of compression balls 212, and engage the back surface 31 of ram extender 30, as shown in FIG. 31. As adapter cleaner 200 is rotated, ram tip bottom cleaning blades 210 clean back surface 31.

Figure 30:
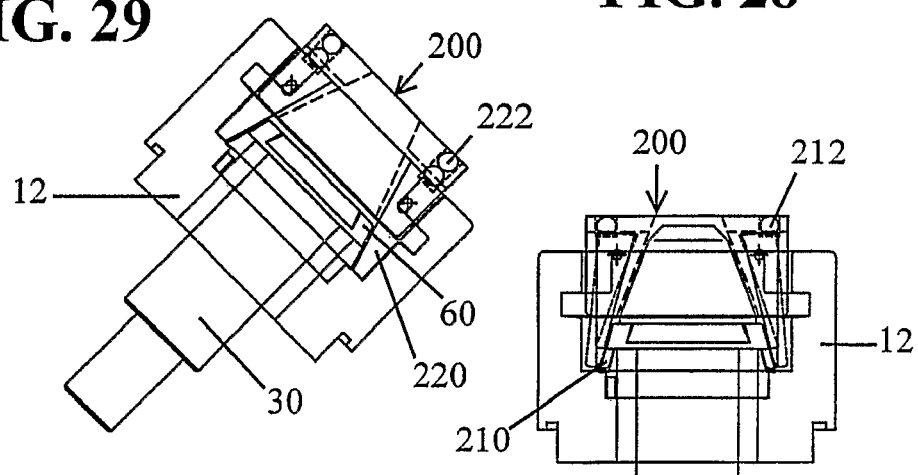
FIG. 30 is a side schematic view of FIG. 28, illustrating the lower level cleaning blades.

Lower level cleaning blades 220 fit within slots in cleaner body 204 and are secured to the cleaner body by pins 224. Cleaning blades 220 extend axially from cleaner body 204. Each cleaning blade 220 has an axially extending slot that engages pin 224. This permits the lower level cleaning blades 220 to move axially. Compression balls 222 bias the lower level cleaning blades into contact with the surfaces of the lifting ring 60 and the adapter body 12 adjacent to shoulder 19, as shown in FIG. 30. When adapter cleaner 200 is rotated, lower level cleaning blades 220 clean the adjacent lower level surfaces of adapter body 12.

It is contemplated that the particular number and arrangement of blades 210, 220, 230, etc. may be dependent upon the particular adapter. Moreover, it is also contemplated that one or more brushes or other cleaning devices may be used in addition to, or in place of, one or more blades 210, 220, 230.

The foregoing disclosure is illustrative of the present invention and is not to be construed as limiting thereof. Although one or more embodiments of the invention have been described, persons of ordinary skill in the art will readily appreciate that numerous modifications could be made without departing from the scope and spirit of the disclosed invention. As such, it should be understood that all such modifications are intended to be included within the scope of this invention. The written description and drawings illustrate the present invention and are not to be construed as limited to the specific embodiments disclosed.

The invention claimed is:

1. A syringe adapter system for a power injector having a drive ram, comprising:
    an adapter body having a front end and a rear end, the front end including a cavity attachable to a syringe, the rear end being attachable to the power injector, the adapter body having a central bore fashioned in the rear end and extending therethrough to the cavity;
    a sealing ring extending around a circumference of the central bore and extending radially inward from the central bore;
    a ram extender receivable within and extendable through the central bore and the sealing ring, wherein the ram extender is attachable to the drive ram; and,
    wherein the sealing ring substantially prevents liquid present in the adapter body from leaking through the central bore into the power injector
    wherein the cavity defines an interior space bounded by one or more side walls and a cavity bottom; and,
    further comprising a drain aperture fashioned radially through a side wall of the adapter body and proximal to the cavity bottom, wherein the drain aperture fluidly communicates liquid in the cavity to drain from the adapter body.

2. A syringe adapter assembly for a power injector, comprising:
    an adapter body having a front end and a rear end, the front end including a cavity adapted to receive a syringe, wherein the cavity defines an interior space bounded by one or more side walls and a cavity bottom, the rear end being attachable to the power injector, the adapter body having a central bore therethrough,
    wherein the adapter body further includes a drain aperture fashioned radially through a side wall thereof and positioned proximal to the cavity bottom, the drain aperture adapted to fluidly communicate liquid present in the interior space to drain from the adapter body.

3. The syringe adapter assembly as recited in claim 2, wherein the central bore of the adapter body extends from the rear end therethrough to the cavity; and,
    further comprising a sealing ring extending into the central bore.

4. The syringe adapter assembly as recited in claim 3, further comprising a ram extender extending through the central bore and through the sealing ring.

5. The syringe adapter assembly as recited in claim 4, further comprising a ram tip cone attached to the ram extender.

6. The syringe adapter assembly as recited in claim 4, wherein the rear end of the adapter body comprises a plurality of threaded apertures, and wherein the assembly further comprises a rear connector plate having a plurality of complementary threaded apertures.

7. The syringe adapter assembly as recited in claim 2, further comprising a lifting ring selectively attached to an interior portion of the adapter body.

8. The syringe adapter assembly as recited in claim 2, further comprising a syringe adapter cleaner that comprises a body and a plurality of cleaning blades.

9. The system as defined in claim 1, further comprising:
   a syringe adapter cleaner for cleaning a plurality of interior surfaces of the adapter body, wherein the syringe adapter cleaner includes:
   a body; and,
   a plurality of cleaning members extending from the body, the cleaning members being complementary to interior surfaces of the adapter body.

10. The system as recited in claim 9, wherein the cleaning members are arranged in sets, each set including at least two members.

11. The system as recited in claim 10, wherein at least one of the sets of cleaning members is biasable radially.

12. The system as recited in claim 10, wherein at least one of the sets of cleaning members extends radially outwardly.

13. The system as recited in claim 12, wherein at least one of the sets of the cleaning members extends axially.

14. The system as recited in claim 10, wherein the number of sets of cleaning members is three.

15. A syringe adapter system for a power injector having a drive ram, comprising:
   an adapter body having a front end attachable to a syringe and a rear end attachable to the power injector, the front end including a cavity bounded by one or more side walls and a bottom wall, wherein the adapter body includes a central bore fashioned in the rear end and extending through to the cavity;
   a lifting ring defining an outer circumference sized for being press fit into the cavity and including a through hole defining an inner circumference, wherein the lifting ring includes a recess fashioned in the lifting ring extending around the inner circumference;
   a sealing ring for insertion into the recess, wherein the sealing ring extends radially inward from the central bore;
   a ram extender receivable within and extendable through the central bore and the sealing ring, wherein the ram extender is attachable to the drive ram, wherein the sealing ring substantially prevents liquid present in the adapter body from leaking through the central bore into the power injector; and,
   wherein a drain aperture is radially fashioned through a side wall of the adapter body and proximal to the bottom wall, wherein the drain aperture is adapted to drain liquid from the cavity.

16. A syringe adapter for a power injector, comprising:
   an adapter body having a front end including a cavity adapted to receive an associated syringe and a rear end adapted to attach to the power injector, the cavity being bounded by one or more walls, the adapter body having a central bore extending from the rear end of the adapter body to the cavity, and
   wherein the adapter body includes a drain aperture fashioned through a wall bounding the cavity for draining fluid from the cavity.

17. The syringe adapter as defined in claim 16, wherein the one or more walls bounding the cavity includes at least one flanged groove for engaging the associated syringe.

* * * * *